(12) United States Patent
Garnick

(10) Patent No.: US 6,217,844 B1
(45) Date of Patent: *Apr. 17, 2001

(54) METHODS FOR DETECTING LESIONS IN DENSE BREAST TISSUE USING LHRH ANTAGONISTS

(75) Inventor: Marc B. Garnick, Brookline, MA (US)

(73) Assignee: Praecis Pharmaceuticals, Inc., Cambridge, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/067,327

(22) Filed: Apr. 27, 1998

(51) Int. Cl.[7] .......................... A61K 51/00; A61M 36/14
(52) U.S. Cl. ........................ 424/1.11; 424/9.1; 424/645; 530/313
(58) Field of Search .................... 424/1.11, 1.37, 424/1.45, 1.65, 1.61, 1.81, 9.1, 9.3, 9.4, 9.5, 9.6, 9.7; 206/569, 570, 223; 552/502; 530/399, 313, 300; 128/922, 662.02, 660.01, 653.1; 430/449; 514/15, 16

(56) References Cited

U.S. PATENT DOCUMENTS

| | | | |
|---|---|---|---|
| 4,431,635 | * 2/1984 | Coy et al. | 424/177 |
| 4,652,441 | * 3/1987 | Okada et al. | 424/19 |
| 4,675,189 | * 6/1987 | Kent et al. | 424/490 |
| 4,677,191 | * 6/1987 | Tanaka et al. | 528/361 |
| 4,689,396 | * 8/1987 | Roeske et al. | 530/313 |
| 4,728,721 | * 3/1988 | Yamamoto et al. | 528/361 |
| 4,801,577 | * 1/1989 | Nestor, Jr. et al. | 514/15 |
| 4,849,228 | * 7/1989 | Yamamoto et al. | 424/457 |
| 4,851,385 | * 7/1989 | Roeske | 514/15 |
| 4,917,893 | * 4/1990 | Okada et al. | 424/423 |
| 4,935,491 | * 6/1990 | Folkers et al. | 530/313 |
| 4,992,421 | * 2/1991 | De et al. | 514/19 |
| 5,003,011 | * 3/1991 | Coy et al. | 530/328 |
| 5,171,835 | * 12/1992 | Janaky et al. | 530/313 |
| 5,296,468 | * 3/1994 | Hoeger et al. | 514/15 |
| 5,300,492 | * 4/1994 | Haviv et al. | 514/15 |
| 5,371,070 | * 12/1994 | Koerber et al. | 514/9 |
| 5,824,286 | * 10/1998 | Hodgen | 424/9.1 |
| 5,843,901 | * 12/1998 | Roeske | 514/5 |
| 5,843,902 | * 12/1998 | Garnick et al. | 514/15 |

OTHER PUBLICATIONS

Andersson et al., "Radiographic patterns of the mamary parenchyma", *Radiol.*, 138:59–62, (1981).

Boyd, N. F. et al., "Quantitative classification of mammorgraphic densities and breast cancer risk: Results from the Canadian national breast screening study", *J. Natl. Cancer Inst.*, 87:670–675, (1995).

Braeuning et al., "New modalities in breast imaging: digital mammography and magnetic resonance imaging", *Breast Cancer Res. Treat.*, 35:31–38, (1995).

Ciatto et al., "A prospective study of the value of mammographic patterns as indicators of breast cancer risk in a screening experience", *Eur. J. Radiol*, 17:122–125, (1993).

Egan et al, "Breast cancer mammography" *Cancer*, 40:2087–2090, (1977).

Harris et al., "Zoladex: endocrine and therapeutic effects in post–menopausal breast cancer", *Br. J. Cancer*, 59:97–99, (1989).

Jackson et al., "Imaging of the radiographically dense breast", *Radiology.*, 188:297–301, (1993).

Jenks, S., "Dense breast tissues may hold increased cancer risk for some", *J. Natl. Cancer Inst.*, 86:578–580, (1994).

Krook et al., "Mammographic parenchymal patterns as a risk indicator for prevalent and incident cancer", *Cancer*, 41:1093–1097, (1978).

Ma et al., "Case–control study of factors associated with failure to detect breast cancer by mammography", *J. Natl. Cancer Inst.*, 84:781–785, (1992).

Oza et al., "Mammographic parenchymal patterns: A marker of breast cancer risk", *Epidemiol. Rev.*, 15:196–208, (1993).

Saftlas et al., "Mammographic parenchymal patterns and breast cancer risk", *Epidemiol. Rev.*, 9:146–174, (1987).

Threatt et al., "Association between mammographic parenchymal pattern classification and incidence of breast cancer", *Cancer*, 45:2550–2556, (1980).

Ursin et al., "Can mammographic densities predict effects of tamoxifen on the breast?", *J. Natl. Cancer Inst.*, 88:128–129, (1996).

v. Gils et al., "Short communication: Breast parenchymal patterns and their changes with age", *Br. J. Radiol*, 68:1133–1135, (1995).

Warner et al., "The risk of breast cancer associated with mammographic parenchymal patterns: A meta–analysis of the published literature to examine the effect of method of classification", *Cancer Detect. Prev.*, 16:67–72, (1992).

Wolfe, J. N., "Risk for breast cancer development determined by mammographic parenchymal pattern", *Cancer*, 37:2486–2492, (1976).

\* cited by examiner

*Primary Examiner*—Dameron Jones
(74) *Attorney, Agent, or Firm*—Lahive & Cockfield, LLP; Giulio A. DeConti, Jr.; Maria C. Laccotripe

(57) ABSTRACT

Improved methods for detecting lesions in dense breast tissue are disclosed. The methods of the invention generally feature administration to a subject of an LHRH antagonist in an amount and for a period of time sufficient to reduce the density of breast tissue prior to generating an image of the breast tissue, for example by mammography, to detect a lesion in the breast tissue. Packaged formulations for reducing breast density in a subject prior to generating an image of the subject's breast tissue, comprising an LHRH antagonist packaged with instructions for using the LHRH antagonist to reduce breast density in a subject prior to imaging the breast tissue, are also disclosed.

22 Claims, No Drawings

METHODS FOR DETECTING LESIONS IN DENSE BREAST TISSUE USING LHRH ANTAGONISTS

BACKGROUND OF THE INVENTION

Breast cancer is one of the most prevalent forms of cancer in women and one of the leading causes of cancer deaths in women. Mammography, or radiographic imaging of breast tissue, has proven to be an effective procedure for detecting and diagnosing early stage breast tumors. As currently performed, however, mammography does not detect all breast cancers. The ability of mammography to detect early stage tumors varies among women, depending on the characteristics of the breast tissue examined. Detection of breast lesions are particularly problematic in women with radiologically "dense" breasts, i.e., breast tissue exhibiting a dense parenchymal pattern upon mammography. The radiographic density of the breast tissue can obscure breast lesions, making detection more difficult and increasing the likelihood that the lesion will be overlooked. Such false negative mammograms result in delay in the diagnosis, and subsequent treatment, of breast cancer.

The problem of detecting lesions in radiologically dense breasts is not a minor one. Approximately 25–50% of women have been reported to have a dense parenchymal pattern upon mammography (see e.g., Threat, B., et al. (1980) *Cancer* 45:2550–2556; Jackson, V. P., et al. (1993) *Radiology* 188:297–301; van Gils, C. H., et al. (1995) *Br. J Radiol.* 68:1133–1135), although the prevalence of dense breasts decreases with age (e.g., to approximately 6% in women over 60, as reported Threat, B., et al., supra). An association between radiologic breast density and an increased risk for breast cancer has been reported in numerous clinical studies (see e.g., Wolfe, J. N. (1976) *Cancer* 37:2486–2492; Krook, P. M., et al. (1978) *Cancer* 41:1093–1097; Threat, B., et al., supra; Andersson, I., et al. (1981) *Radiology* 138:59–62; Saftlas, A. F. and Szklo, M. (1987) *Epidemiol. Rev.* 9:146 174; Warner, E., et al. (1992) *Cancer Det. Prevent.* 16:67–72; Ma, L., et al. (1992) *J. Natl. Cancer Inst.* 84:781–785; Ciatto, S. and Zappa, M. (1993) *Eur. J. Radiol.* 17:122–125; Oza, A. M. and Boyd, N. F. (1993) *Epidemiol. Rev.* 15:196–208; Jenks, S. (1994) *J. Natl. Cancer Inst.* 86:578–580; Boyd, N. F., et al. (1995) *J. Natl. Cancer Inst.* 87:670675). The observed increased cancer risk associated with breast density has been attributed to a combination of 1) breast parenchymal patterns being an actual risk factor in the development of breast tumors and 2) "masking" of early stage tumors in dense breasts (see e.g., Egan, R. I. and Mosteller, R. C. (1977) *Cancer* 40:2087–2090; Saftlas, A. F. and Szklo, M., supra; Oza, A. M. and Boyd, N. F., supra). Because of the reported association between breast density and cancer incidence, women with dense breasts are recommended to have more frequent mammograms, which exposes these women to the additional risks associated with mammography itself.

Few solutions to the problem of imaging the radiographically dense breast have been proposed. Approaches to improve detection of breast lesions in dense breasts have focused on the development of alternative imaging modalities to mammography, such as ultrasonography, transillumination, thermography, computed tomography, magnetic resonance imaging, radionuclide imaging and digital mammography, which may provide better resolution of lesions in dense breasts (see e.g., Jackson, V. P., et al. (1993) *Radiology* 188:297–301; Braeuning, M. P., et al (1995) *Breast Cancer Res. Treat.* 35:31–38). Use of an alternative imaging procedure, however, likely would require large expenditures by health care providers for new equipment and personnel training, which may hinder widespread application of this approach. Additional strategies for improving the detection of lesions in dense breast tissue are still needed, especially strategies that can be used with traditional mammography.

SUMMARY OF THE INVENTION

This invention provides improved methods for detecting lesions in dense breast tissue. The methods of the invention generally feature administration to a subject of a luteinizing hormone releasing hormone (LHRH) antagonist in an amount and for a period of time sufficient to reduce the density of breast tissue prior to imaging the breast tissue, for example by mammography, to detect a lesion in the breast tissue.

In one embodiment, the invention provides a method for reducing breast density in a subject. The method comprises administering to the subject an LHRH antagonist in an amount and for a period of time sufficient to reduce breast density in the subject prior to generating an image of the breast tissue.

In another embodiment, the invention provides a method for detecting a lesion in breast tissue in a subject. This method comprises:

administering to the subject an LHRH antagonist in an amount and for a period of time sufficient to reduce the density of the breast tissue in the subject; and generating an image of the breast tissue such that a lesion in the breast tissue is detected.

The breast lesion to be detected can be, for example, a malignant or benign breast tumor. The image of the breast tissue can be detected, for example, by standard film screen mammography or by an alternative procedure for visualizing breast tissue, such as ultrasonography, transillumination, thermography, computed tomography, magnetic resonance imaging, radionuclide imaging or digital mammography.

The invention further provides a packaged formulation for reducing breast density in a subject prior to generating an image of the subject's breast tissue. This packaged formulation comprises an LHRH antagonist packaged with instructions for using the LHRH antagonist for reducing breast density in the subject prior to generating an image of the subject's breast tissue.

DETAILED DESCRIPTION OF THE INVENTION

The present invention provides methods and compositions for improved detection of lesions in dense breast tissue. The methods of the invention generally feature administration to a subject of an LHRH antagonist in an amount and for a period of time sufficient to reduce breast density in the subject, prior to generating an image of the subject's breast tissue. LHRH is a natural hormone produced by the hypothalamus that interacts with the LHRH receptor (LHRH-R) in the pituitary to stimulate production of luteinizing hormone (LH). LHRH antagonists inhibit the LHRH receptor such that release of LH is inhibited, which ultimately leads to decreased circulating levels of sex hormones (e.g., estrogens in women) and induces a temporary castrate state. While not intending to be limited by mechanism, these decreased levels of circulating estrogens resulting from LHRH antagonist treatment are thought to lead to, or at least contribute to, decreased radiological breast density. This mechanism is consistent with, for example, the observation that breast densities in post-menopausal women are significantly reduced compared to pre-menopausal women.

In order that the invention may be more readily understood, certain terms used herein are first defined.

The term "LHRH antagonist", as used herein, refers to a compound that inhibits the luteinizing hormone releasing hormone receptor such that release of LH is inhibited. LHRH antagonists have been described in the art; see e.g., U.S. Pat. No. 5,470,947 to Folkers et al.; Folkers et al., PCT Publication No. WO 89/01944; U.S. Pat. No. 5,413,990 to Haviv; U.S. Pat. No. 5,300,492 to Haviv; U.S. Pat. No. 5,371,070 to Koerber et al.; U.S. Pat. No. 5,296,468 to Hoeger et al.; U.S. Pat. No. 5,171,835 to Janaky et al.; U.S. Pat. No. 5,003,011 to Coy et al.; U.S. Pat. No. 4,431,635 to Coy; U.S. Pat. No. 4,992,421 to De et al.; U.S. Pat. No. 4,851,385 to Roeske; U.S. Pat. No. 4,801,577 to Nestor, Jr. et al.; and U.S. Pat. No. 4,689,396 to Roeske et al. Preferred LHRH antagonists are those having low histamine-releasing activity (e.g., an $ED_{50}$ for histamine release in a standard in vitro histamine release assay of at least 3 $\mu$g/ml, more preferably at least 5 $\mu$g/ml, and still more preferably at least 10 $\mu$g/ml) and that exhibit water solubility. Preferred LHRH antagonists with low histamine-releasing activity and water solubility include compounds disclosed in U.S. patent application Ser. No. 08/480,494, and corresponding PCT application WO 96/40757, the entire contents of both of which are expressly incorporated herein by reference. An especially preferred LHRH antagonist comprises the structure: Ac-D-Nal$^1$, 4-Cl-D-Phe$^2$, D-Pal$^3$, N-Me-Tyr$^5$, D-Asn$^6$, Lys (iPr)$^8$, D-Ala$^{10}$-LHRH (referred to herein as PPI-149, and described fuirther in WO 96/40757). Histamine-releasing activity of an LHRH antagonist can be assayed by the method described in U.S. Pat. No. 4,851,385 to Roeske. The efficacy of candidate LHRH antagonists in inhibiting LH release can be assayed, for example, in an animal model such as that described in Corbin and Beattie, *Endocrine Res. Commun.* 2:1 (1975). In this assay, the LHRH antagonistic activity of a candidate compound is assayed by measuring the antiovulatory activity (AOA) of the compound in rats.

The term "breast density" is intended to refer to the appearance of the breast parenchyma by mammography. The radiographic appearance of breast tissue varies depending upon the relative amounts of fat, connective tissue and epithelial tissue within the breast. Radiologically, fat appears lucent (ie., a darker appearance), whereas connective and epithelial tissues appear dense (ie., a lighter appearance). The traditional system for classifying breast density is that of Wolfe (*Cancer* (1976) 37:2486–2492), who defined four breast parenchymal patterns. According to Wolfe, N1 signifies an essentially normal breast which is composed almost completely of fat with perhaps a few fibrous connective tissues and no ducts visible; P1 signifies a breast involved with a prominent duct pattern to a minimal degree, typically composed mainly of fat but in the subareolar area (or less commonly in the upper axillary quadrant or other portions of the breast) one can see a beaded linear pattern representing prominent ducts (up to one fourth the volume of the breast), which ducts may vary in diameter from about 1 mm up to 3 or 4 mm in unusual cases; P2 signifies a breast involved with a prominent duct pattern of a moderate to severe degree (more than one fourth the volume of the breast), wherein the ducts very often have a triangular disposition in the central portion of the breast and the degree of involvement may be from one-half the volume of the parenchyma to nearly all of it and the connective tissue hyperplasia is sufficient to produce coalescence of the ducts in some areas; and DY signifies an extremely dense parenchyma, which usually denotes connective tissue hyperplasia. Breast tissues with a parenchymal pattern of P2 or DY using the system of Wolfe are typically considered to be "dense breasts".

Alternative classification systems also can be used to evaluate breast density. For example, Threat et al. (*Cancer* (1980) 45:2550–2556) further refined the Wolfe classification system. In addition to maintaining the N1, P1 and P2 categories, Threat et al. defined additional subdivisions as follows: DY1: homogenous density filling no more than one-half of the breast; DY2: homogenous density filling more than one half of the breast; DY: mixed fatty and dense breasts with prominent ducts visible within the dense areas of the breast, the amount of density varying from under one half to more than one-half of the breast contents but prominent ducts are visible within the densities; and QDY: a specific pattern of very organized, swirly breast tissue, with either organized swirls of lucency with very little associated density (QDY1) or organized swirls of homogeneous density in more than 50% of the breast (QDY2). Breast classified as either DY1, DY2, DY or QDY2 are considered to be "dense breasts", breast classified as P2 are considered to be of "intermediate density" and breast classified as N1, P1 or QDY1 are considered to be "lucent". Computer-assisted measurements can also be used to evaluate and categorize breast densities (e.g., as described in Boyd, N. F., et al (1995) *J. Natl. Cancer Inst.* 87:670–675).

The methods and compositions of the invention "to reduce breast density" or "for reducing breast density" are intended to refer to methods and compositions that cause a change in the breast parenchymal pattern of a subject to a more lucent (ie., less dense) appearance, relative to the breast parenchymal pattern of the subject in the absence of treatment with a method or composition of the invention.

As used herein, the term "subject" is intended to include warm-blooded animals, preferably mammals, more preferably humans and most preferably female humans. Although the invention is described herein in the context of female breast tissue, which is the most preferred embodiment, use of the compositions and methods of the invention in the detection of rare lesions in breast tissue of males is also contemplated.

The term "generating an image of breast tissue" is intended to refer to use of one of a variety of techniques known in the art for visualizing breast architecture. Examples of such techniques include, but are not intended to be limited to, film screen mammography (ie., standard mammography), ultrasonography, transillumination, thermography, computed tomography, magnetic resonance imaging, radionuclide imaging and digital mammography. Standard film screen mammography is performed by procedures well known in the art. Other imaging techniques referred to above, as applied to the visualization of breast architecture, are described in Jackson, V. P., et al. (1993) *Radiology* 188:297–301 and Braeuning, M. P., et al. (1995) *Breast Cancer Res. Treat.* 35:31–38.

The term "breast lesion", or simply "lesion" is intended to refer to any abnormality in breast tissue that can be detected by generating an image of the breast tissue. Examples of such lesions include, but are not intended to be limited to, malignant breast tumors, benign breast tumors and cysts.

One aspect of the invention pertains to methods for reducing breast density in a subject prior to generating an image of breast tissue of the subject. The methods comprise administering to the subject an LHRH antagonist in an amount and for a period of time sufficient to reduce breast density in the subject prior to generating an image of breast tissue of the subject.

The period of time for which the LHRH antagonist is administered may vary depending upon such factors as the particular subject involved, the density of the breast tissue prior to treatment, the particular LHRH antagonist used and the intended result (e.g., the degree of lucency of breast tissue desired). In various preferred embodiments, however, the LHRH antagonist is administered to the subject about one month prior to generating an image of the breast tissue, about one week prior to generating an image of the breast tissue, about one to three days prior to generating an image of breast tissue or about 6 to 24 hours prior to generating an image of breast tissue.

The amount of LHRH antagonist administered also may vary depending upon such factors as the particular subject involved, the density of the breast tissue prior to treatment, the particular LHRH antagonist used and the intended result. A non-limiting range for an amount of an LHRH antagonist sufficient to reduce breast density in a subject is 0.01 µg/kg to 10 mg/kg. In various preferred embodiments, the LHRH antagonist is administered at a dose range of about 5–1000 µg/kg/day, about 10–500 µg/kg/day or about 10–100 µg/kg/day. Preferred dosages include 30 µg/kg/day, 50 µg/kg/day and 100 µg/kg/day.

The treatment regimen also may vary depending upon such factors as the particular subject involved, the density of the breast tissue prior to treatment, the particular LHRH antagonist used and the intended result. For example, the LHRH antagonist may be administered in a single dose, such as a single injection (e.g., a single subcutaneous or intravenous injection). Alternatively, the LHRH antagonist may be administered in multiple doses over time, such as multiple injections (e.g., multiple subcutaneous or intravenous injection). As used herein the terms "multiple doses" and "multiple injections" are intended to mean more than one dose or injection, respectively. For example, the LHRH antagonist may be administered by multiple injections spaced several hours to several days apart, such as 2 to 10 injections spaced 3, 4, 5, 6, 7, 8, 9, 10, 12, 24, 36 or 48 hours apart.

Alternatively, the LHRH antagonist may be administered in a form that allows for continuous release of the LHRH antagonist into the subject over time, such as by continuous infusion (e.g., via a subcutaneous osmotic pump, commercially available from Alzet) or in a sustained-release formulation. As used herein, the term "sustained release formulation" is intended to encompass formulations that allow for the continuous delivery of an LHRH antagonist to a subject over a period of time, preferably from several days to 1–4 weeks to 1–3 months. Such formulations are typically administered subcutaneously or intramuscularly and allow for the continual steady release of a predetermined amount of drug in the subject over time.

In a preferred embodiment, the LHRH antagonist is formulated as a sustained release formulation as described in U.S. application Ser. No. 08/762,747 and corresponding PCT Application No. PCT/US97/22881, the contents of both of which are expressly incorporated herein by reference. In brief, the LHRH antagonist is formulated into a pharmaceutical composition comprising a complex of the LHRH antagonist and a carrier macromolecule that allows for sustained delivery of the LHRH antagonist in vivo upon administration of the complex. This complex is formed by combining the LHRH antagonist and the carrier macromolecule under conditions such that a substantially water-insoluble complex is formed, e.g., aqueous solutions of the LHRH antagonist and carrier macromolecule are mixed until the complex precipitates. The complex may be in the form of a solid (e.g., a paste, granules, a powder or a lyophilizate) or the powdered form of the complex can be pulverized finely enough to form stable liquid suspensions or semi-solid dispersions. The complex is suitable for sterilization, such as by gamma irradiation or electron beam irradiation, prior to administration in vivo. Preferred carrier macromolecules for use in the complex are anionic polymers, such as anionic polyalcohol derivatives, or fragments thereof, and salts thereof (e.g., sodium salts). Anionic moieties with which the polyalcohol can be derivatized include, for example, carboxylate, phosphate or sulfate groups. A particularly preferred anionic polymer is an anionic polysaccharide derivative, or fragment thereof, and salts thereof (e.g., sodium salts). The carrier macromolecule may comprise a single molecular species (e.g., a single type of polymer) or two or more different molecular species (e.g., a mixture of two types of polymers). Examples of specific anionic polymers include carboxymethylcellulose, algin, alginate, anionic acetate polymers, anionic acrylic polymers, xantham gums, sodium starch glycolate, and fragments, derivatives and pharmaceutically acceptable salts thereof, as well as anionic carageenan derivatives, anionic polygalacturonic acid derivatives, and sulfated and sulfonated polystyrene derivatives. A preferred anionic polymer is carboxymethylcellulose sodium salt. In certain embodiments, the carrier macromolecule, preferably carboxymethylcellulose sodium, and the LHRH antagonist, preferably PPI-149, are combined at a ratio of 0.2:1 (w/w) of carrier macromolecule:peptidic compound. In various other embodiments, the ratio of carrier macromolecule to peptidic compound (w/w) can be, for example, 0.5:1, 0.4:1, 0.3:1, 0.25:1, 0.15:1 or 0.1:1.

Alternatively, the sustained-release formulation of LHRH antagonist can be, for example, a formulation comprising a polymer selected from the group consisting of a poly-lactide polymer, a poly-glycolide polymer and a poly-lactide/poly-glycolide copolymer (e.g., the drug is encapsulated within a microcapsule comprising the polymer or copolymer). Such sustained-release formulations, suitable for depot injection, are known in the art for administration of LHRH agonists, such as leuprolide (see e.g., U.S. Pat. No. Nos. 4,677,191 and 4,728,721; suitable formulations are also described further below). The sustained-release formulations can be formulated to allow for delivery of the drug over a predetermined time period.

To achieve sustained treatment for extended periods of time, it may be necessary to readminister a sustained release formulation. For example, a sustained release formulation that delivers the LHRH antagonist for a period of one month can be readministered on a monthly basis to achieve sustained treatment for several months (e.g., 6 months). Similarly, a sustained release formulation that delivers the LHRH antagonist for a period of one week can be readministered on a weekly basis to achieve sustained treatment for several weeks. The sustained release formulations provided herein (see e.g., Example 2) can deliver an LHRH antagonist for a period of at least about one month and thus can be readministered on a monthly basis to achieve extended treatment.

The method of the invention can be used with any of a variety of compounds known in the art to have LHRH antagonist activity, non-limiting examples of which include Nal-Glu (having the structure: Ac-D-Nal(2)$^1$, 4-Cl-D-Phe$^2$, D-Pal$^3$, Arg$^5$, D-Glu$^6$ (AA), D-Ala$^{10}$-LHRH) and SB-75 (also known as Cetrorelix™) (having the structure: Ac-D-

Nal¹, 4-Cl-Phe², D-Pal³, D-Cit⁶, D-Ala¹⁰-LHRH). LHRH antagonists typically are analogues of the LHRH decapeptide. Another example of an LHRH antagonist that can be used in the method of the invention has the structure: Ac-D-Nal¹, 4-Cl-D-Phe², D-Pal³, N-Me-Tyr⁵, D-Lys(N-epsilon-nicotinoyl)⁶, Lys(iPr)⁸, D-Ala¹⁰-LHRH (described further in European Patent EP 400 065 B)

A particularly preferred LHRH antagonist for use in the methods of the invention has the following structure: Ac-D-Nal¹, 4-Cl-D-Phe², D-Pal³, N-Me-Tyr⁵, D-Asn⁶, Lys (iPr)⁸, D-Ala¹⁰-LHRH (referred to herein as PPI-149).

PPI-149 exhibits low histamine releasing activity and high solubility. Moreover, upon administration, PPI-149 rapidly reduces sex hormone levels to castrate levels. For example, when a single dose of PPI-149 was administered to male rats at a dosage of 300 or 1000 µg/kg, plasma testosterone levels were decreased to nearly undetectable levels by 6 hours post-administration. Testosterone levels returned to normal by 24 hours after the 300 µg/kg dose, but not until 72 hours after the 1000 µg/kg dose. When PPI-149 was administered in eight intravenous doses of 1, 10 or 100 µg/kg, each every three hours (corresponding respectively to 8, 80 or 800 µg/kg/day), castrate levels of testosterone were achieved at doses of 10 µg/kg every three hours. A dose as low as 1 µg/kg (equivalent to 8 µg/kg/day) induced a significant decrease in plasma testosterone levels. Continuous subcutaneous infusion, via an osmotic pump, of PPI-149 for two weeks at dosages of 300 or 1000 µg/kg/day ("high dose"), followed by an additional two weeks with 5, 15 or 50 µg/kg/day ("low dose"), resulted in castrate levels of testosterone within the first 7 days (and presumably within the first 24 hours) with either of the two initial high doses, and this castration level was maintained by all three subsequent low doses for an additional 21 days. Recovery of testosterone levels following pump removal was complete within two weeks.

Another aspect of the invention pertains to methods for detecting a lesion in breast tissue of a subject. The methods comprise:
administering to the subject an LHRH antagonist in an amount and for a period of time sufficient to reduce the density of the breast tissue of the subject; and
generating an image of the breast tissue such that a lesion in the breast tissue is detected.

Preferably, the lesion to be detected by the method is a tumor, such as a malignant or benign tumor. The image of the breast tissue can be generated by any one of a variety of techniques known in the art for visualizing breast architecture, examples of which include, but are not intended to be limited to, film screen mammography (i.e. standard mammography), ultrasonography, transillumination, thermography, computed tomography, magnetic resonance imaging, radionuclide imaging and digital mammography. In a preferred embodiment, the image of the breast tissue is generated by standard film screen mammography.

As described above for the methods of reducing breast density, in the methods of the invention for detecting a lesion in breast tissue, the time period for administering the LHRH antagonist may depend upon a number of varying factors (discussed above), but in various embodiments the LHRH antagonist is administered to the subject about one month prior to generating an image of the breast tissue, about one week prior to generating an image of the breast tissue, about one to three days prior to generating an image of breast tissue or about 6 to 24 hours prior to generating an image of breast tissue.

Also as described above for the methods of reducing breast density, in the methods of the invention for detecting a lesion in breast tissue, the amount of LHRH antagonist administered may depend upon a number of varying factors (discussed above), but in various embodiments the LHRH antagonist is administered at a dose range of about 5–1000 µg/kg/day, about 10–500 µg/kg/day or about 10–100 µg/kg/day. A non-limiting range for an amount of an LHRH antagonist sufficient to reduce breast density in a subject is 0.01 µg/kg to 10 mg/kg. Preferred dosages include 30 µg/kg/day, 50 µg/kg/day and 100 µg/kg/day.

Also as described above for the methods of reducing breast density, in the methods of the invention for detecting a lesion in breast tissue, the treatment regimen for LHRH antagonist administration may depend upon a number of varying factors (discussed above), but in various embodiments the LHRH antagonist is administered in a single injection, by multiple injections, by continuous infusion or in a sustained-release formulation.

Another aspect of the invention pertains to a packaged formulation for reducing breast density in a subject prior to generating an image of breast tissue of the subject. This packaged formulation comprises an LHRH antagonist packaged with instructions for using the LHRH antagonist for reducing breast density in a subject prior to generating an image of breast tissue of the subject. In one embodiment, the LHRH antagonist within the packaged formulation is in a form suitable for subcutaneous or intravenous injection. In another embodiment, the LHRH antagonist within the packaged formulation is in a form suitable for continuous infusion. In yet another embodiment, the LHRH antagonist within the packaged formulation is in a sustained-release formulation.

LHRH antagonists suitable for use in the methods and packaged formulations of the invention can be incorporated into pharmaceutical compositions suitable for administration to a subject. Preferably, the pharmaceutical composition comprises an LHRH antagonist and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous or parenteral administration (e.g., by injection). Depending on the route of administration, the active compound may be coated in a material to protect the compound from the action of acids and other natural conditions which may inactivate the compound.

An LHRH antagonist can be administered by a variety of methods known in the art. In one embodiment, the LHRH antagonist is administered in a time release formulation (also referred to as a sustained-release formulation), for example in a composition which includes a slow release polymer, or a composition suitable for depot injection. The active compounds can be prepared with carriers that will protect the compound against rapid release, such as a controlled release formulation, including implants, transdermnal patches, and microencapsulated delivery systems. A particularly preferred sustained release formulation comprises an LHRH antagonist, preferably PPI-149, complexed with an anionic polymer, preferably carboxymethylcellulose, as described further above. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978. Formulations include controlled-release compositions such as are known in the art for the administration of leuprolide (trade name: Lupron®), e.g., microcapsules (U.S. Pat. No. Nos. 4,652,441 and 4,917,893), injectable formulations (U.S. Pat. No. 4,849,228), lactic acid-glycolic acid copolymers useful in making microcapsules or injectable formulations (U.S. Pat. No. Nos. 4,677,191 and 4,728,721), and sustained-release compositions for water-soluble polypeptides (U.S. Pat. No. 4,675,189).

When appropriately formulated, an LHRH antagonist may be orally administered, for example, with an inert diluent or an assimilable edible carrier. The LHRH antagonist (and other ingredients may also be enclosed in a hard or soft shell gelatin capsule, compressed into tablets, or incorporated directly into the subject's diet. For oral therapeutic administration, the LHRH antagonist may be incorporated with excipients and used in the form of ingestible tablets, buccal tablets, troches, capsules, elixirs, suspensions, syrups, wafers, and the like. The percentage of the LHRH antagonist in the compositions and preparations may, of course, be varied.

To administer an LHRH antagonist by other than parenteral administration, it may be necessary to coat the compound with, or co-administer the compound with, a material to prevent its inactivation. For example, the LHRH antagonist may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) *J. Neuroimmunol.* 7:27). Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

LHRH antagonist compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

Sterile injectable solutions can be prepared by incorporating the active compound (e.g., LHRH antagonist) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. Sustained release formulations comprising a complex of the LHRH antagonist and carrier macromolecule (such as the PPI-149/carboxymethylcellulose complex described above) also can be sterilized by, for example, gamma irradiation or electron beam irradiation, prior to administration in vivo.

This invention is further illustrated by the following examples, which should not be construed as limiting. The contents of all references, patents and published patent applications cited throughout this application are hereby incorporated by reference.

EXAMPLE 1

An LHRH antagonist, such as Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH (PPI-149), is administered to a female subject at a dosage of about 5–1000 µg/kg, more preferably about 10–100 µg/kg, by a route and for a period of time sufficient to reduce the density of breast tissue. Subsequently, an image of the breast tissue is obtained by, for example, standard film screen mammography.

EXAMPLE 2

To prepare a sustained release LHRH antagonist formulation, a 100 ml solution of the LHRH antagonist PPI-149 was prepared by dissolving 6.25 mg/ml of PPI-149 in water. An equal sample (100 ml minimum) of USP carboxymethylcellulose sodium (CMC) (low viscosity grade, Hercules Chemical Co.) was prepared at 0.125% w/v and mixed until dissolved. Equal portions of the PPI-149 and CMC solutions were mixed (giving a CMC:peptide ratio of 0.2:1 (w/w)) and a solid material was obtained. The solid material was stirred overnight and then collected by filtration over a 0.45 micron nylon filter. HPLC evaluation of the solution filtrate indicated at least 95% of the PPI-149 compound was converted to the solid complex. was removed from solution. The recovered white paste was rinsed twice with water and then transferred to a vial and dried in vacuo. Upon drying for 72 hours, 633 mg of a white powder was obtained. The solid material was then powdered in a mortar and pestle. Elemental analysis indicated 57% peptide in the complex.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for reducing breast density in a subject prior to generating an image of breast tissue of the subject, comprising administering to the subject an LHRH antagonist in an effective amount prior to generating an image of breast tissue of the subject, thereby reducing breast density in a subject prior to generating an image of breast tissue of the subject, wherein the LHRH antagonist is administered to the subject via a single administration of a sustained release formulation which allows for the continuous delivery of the LHRH antagonist to the subject over 1–3 months.

2. A method for reducing breast density in a subject prior to generating an image of breast tissue of the subject, comprising administering to the subject an LHRH antagonist in an effective amount prior to generating an image of breast tissue of the subject, thereby reducing breast density in a subject prior to generating an image of breast tissue of the subject, wherein the LHRH antagonist is administered to the subject via a single administration of a sustained release formulation which allows for the continuous delivery of the LHRH antagonist to the subject for about 1 month.

3. A packaged formulation for reducing breast density in a subject prior to generating an image of breast tissue of the subject, comprising:
an LHRH antagonist in a pharmaceutical composition, packaged with instructions for using the LHRH antagonist for reducing breast density in a subject prior to generating an image of breast tissue of the subject, wherein the pharmaceutical composition is a sustained release formulation which allows for the continuous delivery of the LHRH antagonist to the subject over 1–3 months.

4. A packaged formulation for reducing breast density in a subject prior to generating an image of breast tissue of the subject, comprising:
an LHRH antagonist in a pharmaceutical composition, packaged with instructions for using the LHRH antagonist for reducing breast density in a subject prior to generating an image of breast tissue of the subject, wherein the pharmaceutical composition is a sustained release formulation which allows for the continuous delivery of the LHRH antagonist to the subject for about 1 month.

5. A method for reducing breast density in a subject prior to generating an image of breast tissue of the subject, comprising administering to the subject an LHRH antagonist in an effective amount prior to generating an image of breast tissue of the subject, thereby reducing breast density in a subject prior to generating an image of breast tissue of the subject, wherein the LHRH antagonist is administered to the subject via a single administration of a sustained release formulation which allows for the continuous delivery of the LHRH antagonist to the subject for 11 days to 4 weeks.

6. A method for reducing breast density in a subject prior to generating an image of breast tissue of the subject, comprising administering to the subject an LHRH antagonist in an effective amount prior to generating an image of breast tissue of the subject, thereby reducing breast density in a subject prior to generating an image of breast tissue of the subject, wherein the LHRH antagonist is administered to the subject in a pharmaceutical composition comprising a solid ionic complex of the LHRH antagonist and a carrier macromolecule.

7. The method of claim 6, wherein the LHRH antagonist and the carrier macromolecule are present in the solid ionic complex at a weight ratio of carrier macromolecule:antagonist selected from the group consisting of 0.5:1, 0.4:1, 0.3:1, 0.25:1, 0.2:1, 0.15:1, and 0.1:1.

8. A method for reducing breast density in a subject prior to generating an image of breast tissue of the subject, comprising administering to the subject an LHRH antagonist in an effective amount prior to generating an image of breast tissue of the subject, wherein the LHRH antagonist is administered to the subject in a pharmaceutical composition comprising a solid ionic complex of the LHRH antagonist and a carrier macromolecule.

9. The method of claim 8, wherein the LHRH antagonist content of the solid ionic complex is selected from the group consisting of 57%, 66%, 77%, and 79% by weight.

10. A packaged formulation for reducing breast density in a subject prior to generating an image of breast tissue of the subject, comprising:
an LHRH antagonist in a pharmaceutical composition, packaged with instructions for using the LHRH antagonist for reducing breast density in a subject prior to generating an image of breast tissue of the subject, wherein the pharmaceutical composition is a sustained release formulation which allows for the continuous delivery of the LHRH antagonist to the subject for 11 days to 4 weeks.

11. A packaged formulation for reducing breast density in a subject prior to generating an image of breast tissue of the subject, comprising:
an LHRH antagonist in a pharmaceutical composition comprising a solid ionic complex of the LHRH antagonist and a carrier macromolecule, packaged with instructions for using the LHRH antagonist for reducing breast density in a subject prior to generating an image of breast tissue of the subject.

12. The packaged formulation of claim 11, wherein the LHRH antagonist and the carrier macromolecule are present in the solid ionic complex at a weight ratio of carrier macromolecule:antagonist selected from the group consisting of 0.5:1, 0.4:1, 0.3:1, 0.25:1, 0.2:1, 0.15:1, and 0.1:1.

13. A packaged formulation for reducing breast density in a subject prior to generating an image of breast tissue of the subject, comprising:
an LHRH antagonist in a pharmaceutical composition comprising a solid ionic complex of the LHRH antagonist and a carrier macromolecule present, packaged with instructions for using the LHRH antagonist for reducing breast density in a subject prior to generating an image of breast tissue of the subject.

14. The packaged formulation of claim 13, wherein the LHRH antagonist content of the solid ionic complex is selected from the group consisting of 57%, 66%, 77%, and 79% by weight.

15. The method of any one of claims 1, 2, 5, 6, or 8, wherein the LHRH antagonist is administered at a dosage range of about 5–1000 $\mu$g/kg/day.

16. The method of any one of claims 1, 2, 5, 6, or 8, wherein the LHRH antagonist is administered at a dosage range of about 10–500 $\mu$g/kg/day.

17. The method of any one of claims 1, 2, 5, 6, or 8, wherein the LHRH antagonist is administered at a dosage range of about 10–100 $\mu$g/kg/day.

18. The method of any one of claims 1, 2, 5, 6, or 8, wherein the LHRH antagonist has the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH.

19. The method of any one of claims 1, 2, 5, 6, or 8, which further comprises generating an image of the breast tissue.

20. The method of claim 19, wherein the image of the breast tissue is generated by film screen mammography.

21. The method of claim 19, wherein the image of the breast tissue is generated by a procedure selected from the group consisting of ultrasonography, transillumination, thermography, computed tomography, magnetic resonance imaging, radionuclide imaging and digital mammography.

22. The packaged formulation of any one of claims 3, 4, 10, 11, or 13, wherein the LHRH antagonist has the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH.

* * * * *

UNITED STATES PATENT AND TRADEMARK OFFICE
CERTIFICATE OF CORRECTION

PATENT NO. : 6,217,844 B1
DATED : April 17, 2001
INVENTOR(S) : Marc B. Garnick

It is certified that error appears in the above-identified patent and that said Letters Patent is hereby corrected as shown below:

Column 3,
Line 32, please delete the word "fuirther" and insert -- further --.

Column 6,
Line 43, please remove the word "No." after the word "Pat."

Column 8,
Line 58, please delete the word "transdermnal" and insert -- transdermal --.

Column 9,
Line 10, please remove the word "No." after ther word "Pat."

Column 11,
Lines 56-63, please delete claim 8.

Lines 56-66, should read :
--      8. The method of claim 2, wherein the LHRH antagonist is administered at a dosage range of about 5-1000 $\mu$g/kg/day.

9. (Amended) The method of claim [42] 6, wherein the LHRH antagonist content of the solid ionic complex is selected from the group consisting of 57%, 66%, 77%, and 79% by weight.

Lines 64-66, should read -- The method of claim 6, wherein the LHRH antagonist content of the solid ionic complex is selected from the group consisting of 57%, 66%, 77%, and 79% by weight. --

UNITED STATES PATENT AND TRADEMARK OFFICE
CERTIFICATE OF CORRECTION

PATENT NO. : 6,217,844 B1
DATED : April 17, 2001
INVENTOR(S) : Marc B. Garnick

It is certified that error appears in the above-identified patent and that said Letters Patent is hereby corrected as shown below:

Column 12,
Lines 26-34, please delete claim 13.
Lines 26-54, should read :
--       13. The method of claim 5, wherein the LHRH antagonist is administered at a dosage range of about 5-1000 µg/kg/day.

14. The packaged formulation of claim [47] 11, wherein the LHRH antagonist content of the solid ionic complex is selected from the group consisting of 57%, 66%, 77%, and 79% by weight.

15. The method of [any one of claims 1, 5, 39, 40, or 42] claim 1, wherein the LHRH antagonist is administered at a dosage range of about 5-1000 µg/kg/day.

16. The method of [any one of claims 1, 5, 39, 40, or 42] claim 1, wherein the LHRH antagonist is administered at a dosage range of about 10-500 µg/kg/day.

17. The method of [any one of claims 1, 5, 39, 40, or 42] claim 1, wherein the LHRH antagonist is administered at a dosage range of about 10-100 µg/kg/day.

18. The method of [any one of claims 1, 5, 39, 40, or 42] claim 1, wherein the LHRH antagonist has the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH.

19. The method of [any one of claims 1, 5,39, 40, or 42,] claim 1, which further comprises generating an image of the breast tissue.

Lines 35-38, should read -- The packaged formulation of claim 11, wherein the LHRH antagonist content of the solid ionic complex is selected from the group consisting of 57%, 66%, 77%, and 79% by weight. --
Lines 39, 42, 45, 48 and 52, please delete the words "any one of claims 1, 2, 5, 6, or 8," and insert -- claim 1 --.
Lines 61-62, please delete the words "any one of claims 3, 4, 10, 11, or 13," and insert -- claim 1 --.

UNITED STATES PATENT AND TRADEMARK OFFICE
CERTIFICATE OF CORRECTION

PATENT NO.    : 6,217,844 B1
DATED         : April 17, 2001
INVENTOR(S)   : Marc B. Garnick It is certified that error appears in the above-identified patent and that said Letters Patent is hereby corrected as shown below:

Lines 62-65 should read:
--     22. The packaged formulation of [any one of claims 27, 32, 44, 45, or 47] claim 3, wherein the LHRH antagonist has the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH.

Line 66 should read:
--     23. The method of claim 6, wherein the LHRH antagonist is administered at a dosage range of about 5-1000 $\mu$g/kg/day.

24. The method of claim 2, wherein the LHRH antagonist is administered at a dosage range of about 10-500 $\mu$g/kg/day.

25. The method of claim 5, wherein the LHRH antagonist is administered at a dosage range of about 10-500 $\mu$g/kg/day.

26. The method of claim 6, wherein the LHRH antagonist is administered at a dosage range of about 10-500 $\mu$g/kg/day.

27. The method of claim 2, wherein the LHRH antagonist is administered at a dosage range of about 10-100 $\mu$g/kg/day.

28. The method of claim 5, wherein the LHRH antagonist is administered at a dosage range of about 10-100 $\mu$g/kg/day.

29. The method of claim 6, wherein the LHRH antagonist is administered at a dosage range of about 10-100 $\mu$g/kg/day.

30. The method of claim 2, wherein the LHRH antagonist has the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH.

31. The method of claim 5, wherein the LHRH antagonist has the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH.

32. The method of claim 6, wherein the LHRH antagonist has the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH.

33. The method of claim 2, which further comprises generating an image of the breast tissue.

UNITED STATES PATENT AND TRADEMARK OFFICE
CERTIFICATE OF CORRECTION

PATENT NO. : 6,217,844 B1
DATED : April 17, 2001
INVENTOR(S) : Marc B. Garnick

It is certified that error appears in the above-identified patent and that said Letters Patent is hereby corrected as shown below:

34. The method of claim 33, wherein the image of the breast tissue is generated by film screen mammography.

35. The method of claim 33, wherein the image of the breast tissue is generated by a procedure selected from the group consisting of ultrasonography, transillumination, thermography, computed tomography, magnetic resonance imaging, radionuclide imaging and digital mammography.

36. The method of claim 5, which further comprises generating an image of the breast tissue.

37. The method of claim 36, wherein the image of the breast tissue is generated by film screen mammography.

38. The method of claim 36, wherein the image of the breast tissue is generated by a procedure selected from the group consisting of ultrasonography, transillumination, thermography, computed tomography, magnetic resonance imaging, radionuclide imaging and digital mammography.

39. The method of claim 6, which further comprises generating an image of the breast tissue.

40. The method of claim 39, wherein the image of the breast tissue is generated by film screen mammography.

41. The method of claim 39, wherein the image of the breast tissue is generated by a procedure selected from the group consisting of ultrasonography, transillumination, thermography, computed tomography, magnetic resonance imaging, radionuclide imaging and digital mammography.

42. The packaged formulation of claim 4, wherein the LHRH antagonist has the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH.

43. The packaged formulation of claim 10, wherein the LHRH antagonist has the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH.

UNITED STATES PATENT AND TRADEMARK OFFICE
CERTIFICATE OF CORRECTION

PATENT NO.    : 6,217,844 B1
DATED         : April 17, 2001
INVENTOR(S)   : Marc B. Garnick It is certified that error appears in the above-identified patent and that said Letters Patent is hereby corrected as shown below:

44. The packaged formulation of claim 11, wherein the LHRH antagonist has the following structure: Ac-D-Nal$^1$, 4-Cl-D-Phe$^2$, D-Pal$^3$, N-Me-Tyr$^5$, D-Asn$^6$, Lys(iPr)$^8$, D-Ala$^{10}$-LHRH. --

Signed and Sealed this

Ninth Day of July, 2002

*Attest:*

*Attesting Officer*

JAMES E. ROGAN
*Director of the United States Patent and Trademark Office*